(12) United States Patent
Hata

(10) Patent No.: US 8,298,297 B2
(45) Date of Patent: Oct. 30, 2012

(54) HAIR-TREATMENT COMPOSITION AND HAIR-TREATMENT METHOD USING SAME

(75) Inventor: Masakatsu Hata, Aichi-ken (JP)

(73) Assignee: Hoyu Co., Ltd., Aichi-Ken (JP)

( * ) Notice: Subject to any disclaimer, the term of this patent is extended or adjusted under 35 U.S.C. 154(b) by 0 days.

(21) Appl. No.: 13/376,499

(22) PCT Filed: Jun. 10, 2010

(86) PCT No.: PCT/JP2010/059874
§ 371 (c)(1),
(2), (4) Date: Dec. 6, 2011

(87) PCT Pub. No.: WO2010/143696
PCT Pub. Date: Dec. 16, 2010

(65) Prior Publication Data
US 2012/0080045 A1    Apr. 5, 2012

(30) Foreign Application Priority Data
Jun. 12, 2009    (JP) ................. 2009-141538

(51) Int. Cl.
*C09B 67/10*    (2006.01)
*A61Q 5/00*    (2006.01)
(52) U.S. Cl. ............. 8/525; 8/526; 8/606; 424/70.21; 424/70.31
(58) Field of Classification Search ............. 8/525, 526, 8/606; 424/70.21, 70.31
See application file for complete search history.

(56) References Cited

U.S. PATENT DOCUMENTS
2007/0265181 A1 * 11/2007 Kikuchi et al. ............. 510/125

FOREIGN PATENT DOCUMENTS
| JP | 06-206810 | 7/1994 |
| JP | 2001-131034 | 5/2001 |
| JP | 2005-041844 | 2/2005 |
| JP | 2006-022085 | 1/2006 |
| JP | 2007-302736 | 11/2007 |
| JP | 2008-266184 | 11/2008 |

OTHER PUBLICATIONS

STIC Search Report dated Apr. 25, 2012.*
The translation of the International Preliminary Report on Patentability mailed Aug. 24, 2010 for International Application No. PCT/JP2010059874. Filed Jun. 10, 2010.

* cited by examiner

*Primary Examiner* — Eisa Elhilo
(74) *Attorney, Agent, or Firm* — Seager, Tufte & Wickhem LLC

(57) ABSTRACT

Provided is a hair-treatment composition containing an amphoteric surfactant having a structure represented by general formula (1) below, and a sugar nonionic surfactant. In general formula (1), $R^1$ represents an alkyl group the carbon number of which is 6 to 20; $R^2$ represents a methyl group, an ethyl group, or a hydroxyethyl group; $R^3$ represents a methyl group, an ethyl group, or a —$CH_2COOH$ group; and n is an integer from 1 to 3.

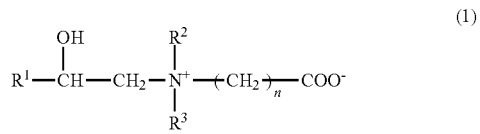

(1)

4 Claims, No Drawings

HAIR-TREATMENT COMPOSITION AND HAIR-TREATMENT METHOD USING SAME

TECHNICAL FIELD

The present invention relates to a hair-treatment composition containing a carboxybetaine-type amphoteric surfactant, and to a hair-treatment method which uses the same.

BACKGROUND ART

Patent Document 1 discloses novel carboxybetaine-type amphoteric surfactants. When hair-treatment compositions containing such amphoteric surfactants are used on dyed keratin fibers, they exhibit a color-retaining effect, that is, a color fade suppressing effect, on the dyed keratin fibers.
Patent Document 1: Japanese Laid-Open Patent Publication No. 2006-22085

SUMMARY OF THE INVENTION

Problems to be Solved by the Invention

It is useful both to increase the foaming properties of hair-treatment compositions containing a carboxybetaine-type amphoteric surfactant, and to enhance the color fade suppressing effect by the hair-treatment compositions. However, Patent Document 1 states only that viscosity adjustment is possible by using a carboxybetaine-type amphoteric surfactant in combination with another surfactant.

Accordingly, one objective of the invention is to provide a hair-treatment composition which has high foaming properties and also has a high dyed hair color fade suppressing effect. Another objective of the invention is to provide a hair-treatment method which uses such a composition.

Means for Solving the Problems

To achieve the foregoing objective and in accordance with a first aspect of the present invention, a hair-treatment composition is provided that includes:

(A) an amphoteric surfactant having a structure represented by the following general formula (1)

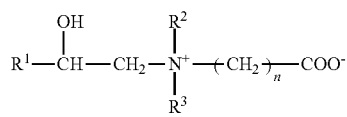

(where $R^1$ represents an alkyl group the carbon number of which is 6 to 20; $R^2$ represents a methyl group, an ethyl group, or a hydroxyethyl group; $R^3$ represents a methyl group, an ethyl group, or a —$CH_2COOH$ group; and n is an integer from 1 to 3);

(B) a sugar nonionic surfactant.

The sugar nonionic surfactant is preferably of at least one type selected from the group consisting of sugar ester surfactants and alkyl glycosides.

The hair-treatment composition according to the above first aspect of the invention is adapted for use in a post-treatment for hair after the hair is dyed with, for example, an oxidative hair dye.

In accordance with a second aspect of the present invention, a hair-treatment method is provided that includes applying the hair-treatment composition according to the above described first aspect to hair in a wet state immediately after the hair is dyed with an oxidative hair dye.

The hair-treatment method may include, following application of the hair-treatment composition to hair: washing and drying the hair; and applying the same hair-treatment composition again to the washed and dried hair.

Effects of the Invention

The invention thus provides a hair-treatment composition which has high foaming properties and has a high dyed hair color fade suppressing effect, and also provides a hair-treatment method which uses such a composition.

MODE FOR CARRYING OUT THE INVENTION

Herein below, one embodiment of the present invention will be described.

A hair-treatment composition according to this embodiment contains (A) an amphoteric surfactant having a structure of general formula (1) below.

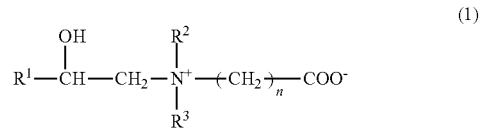

In general formula (1), $R^1$ represents an alkyl group the carbon number of which is 6 to 20; $R^2$ represents a methyl group, an ethyl group, or a hydroxyethyl group; $R^3$ represents a methyl group, an ethyl group, or a —$CH_2COOH$ group; and n is an integer from 1 to 3.

The hair-treatment composition additionally contains (B) a sugar nonionic surfactant.

The amphoteric surfactant functions to suppress the color fading of dyed hair. Specific examples of the amphoteric surfactant include amphoteric surfactants commercially available under the International Nomenclature Cosmetic Ingredient (INCI) name of $C_{12\text{-}14}$ hydroxyalkyl hydroxyethyl sarcosine.

The content of the amphoteric surfactant in the hair-treatment composition is preferably from 0.01 to 30% by mass, more preferably from 0.05 to 20% by mass, and even more preferably from 0.1 to 10% by mass. When the content of the amphoteric surfactant is 0.01% by mass or higher, a pronounced dyed hair color fade suppressing effect is easily obtained. However, the content of this amphoteric surfactant in excess of 30% by mass is not cost-effective.

Sugar nonionic surfactants have the function of increasing the actions and effects of the above amphoteric surfactant and also of increasing the foaming properties of the hair-treatment composition. Sugar nonionic surfactants have a sugar moiety which is a hydrophilic group. The sugar nonionic surfactant used is preferably of at least one type selected from sugar ester surfactants and alkyl glycosides. Specific examples of sugar ester surfactants include sucrose fatty acid esters and sorbitan fatty acid esters.

Specific examples of sucrose fatty acid esters include sucrose fatty acid monoesters and sucrose fatty acid polyesters. Specific examples of sucrose fatty acid monoesters include sucrose stearate, sucrose palmitate, sucrose myristate, sucrose oleate, sucrose laurate, and sucrose coconut oil fatty acid monoester. Specific examples of sucrose fatty acid polyesters include sucrose polylaurate.

Specific examples of sorbitan fatty acid esters include sorbitan monooleate, sorbitan sesquioleate, sorbitan trioleate, sorbitan monostearate, sorbitan monopalmitate, sorbitan monolaurate, polyoxyethylene (abbreviated below as "POE") sorbitan monooleate, POE sorbitan monostearate (e.g., Polysorbate-60), POE sorbitan monopalmitate, POE sorbitan monolaurate, POE sorbitan trioleate, POE sorbitol tetraoleate, POE sorbitol hexastearate, POE sorbitol monolaurate, and POE sorbitol beeswax.

Specific examples of alkyl glucosides include octyl glucoside, nonyl glucoside, decyl glucoside, octyl maltoside, octyl thioglucoside, lauryl glucoside, and coconut oil alkyl glucoside. The sugar nonionic surfactant used may be of one type only, or two or more types of sugar nonionic surfactants may be used in combination.

The content of sugar nonionic surfactant in the hair-treatment composition is preferably from 0.01 to 20% by mass, more preferably from 0.05 to 15% by mass, and even more preferably from 0.1 to 10% by mass. When the content of the sugar nonionic surfactant is 0.01% by mass or higher, a pronounced dyed hair color fade-suppressing effect and a pronounced hair-treatment composition foaming property-increasing effect are easily obtained. However, when the content of the sugar nonionic surfactant is greater than 20% by mass, hair that has been washed and dried following treatment with the hair-treatment composition may become sticky.

The hair-treatment composition may optionally include also, for example, any of water, lower alcohols, water-soluble copolymeric compounds, oil-based ingredients, polyhydric alcohols, additional surfactants, sugars, preservatives, stabilizers, pH adjustors, plant and microbial extracts, protein hydrolyzates, crude drug extracts, vitamins, fragrances, antioxidants, ultraviolet absorbers, chelating agents, and inorganic salts.

Water and lower alcohols serve as solvents or dispersants for the various ingredients in the hair-treatment composition.

Water-soluble polymeric compounds that may be used include anionic, cationic, nonionic, or amphoteric polymeric compounds. Any such compound that is a natural compound or a synthetic compound may be used. Specific examples of cationic water-soluble polymeric compounds include poly(dimethylmethylenepiperidinium chloride) liquids, hydroxyethyl cellulose dimethyldiallylammonium chloride, polyquaternium-10, and cationized guar gum. Specific examples of nonionic water-soluble synthetic polymeric compounds include hydroxyethyl cellulose and polyethylene glycol. Specific examples of amphoteric water-soluble synthetic polymeric compounds include polyquaternium-22, polyquaternium-39, and polyquarternium-47.

Specific examples of oil-based ingredients include oils and fats, waxes, higher alcohols, hydrocarbons, higher fatty acids, alkyl glyceryl ethers, esters, and silicones.

Specific examples of oils and fats include lanolin, olive oil, camellia oil, shear nut oil, almond oil, safflower oil, sunflower oil, soybean oil, cottonseed oil, sesame oil, corn oil, rapeseed oil, rice bran oil, rice germ oil, grapeseed oil, avocado oil, macadamia nut oil, castor oil, coconut oil, and evening primrose oil.

Specific examples of waxes include beeswax, candelilla wax, carnauba wax, jojoba wax, and lanoline.

Specific examples of higher alcohols include cetyl alcohol (cetanol), 2-hexyldecanol, stearyl alcohol, isostearyl alcohol, cetostearyl alcohol, oleyl alcohol, arachyl alcohol, behenyl alcohol, 2-octyldodecanol, lauryl alcohol, myristyl alcohol, decyltetradecanol, and lanolin alcohol.

Specific examples of hydrocarbons include paraffins, olefin oligomers, polyisobutene, hydrogenated polyisobutene, mineral oils, squalane, polybutene, polyethylene, microcrystalline wax, and vaseline.

Specific examples of higher fatty acids include lauric acid, myristic acid, palmitic acid, stearic acid, behenic acid, isostearic acid, 12-hydroxystearic acid, oleic acid, and lanoline fatty acids.

Specific examples of alkyl glyceryl ethers include batyl alcohol, chimyl alcohol, selachyl alcohol, and isostearyl glyceryl ether.

Specific examples of esters include diisopropyl adipate, isopropyl myristate, cetyl octanoate, isononyl isononanoate, octyldodecyl myristate, isopropyl palmitate, stearyl stearate, myristyl myristate, isotridecyl myristate, 2-ethylhexyl palmitate, octyldodecyl ricinoleate, cholesteryl/lanosteryl fatty acids the carbon number of which is 10 to 30, cetyl lactate, lanoline acetate, ethylene glycol di-2-ethylhexanoate, fatty acid esters of pentaerythritol, fatty acid esters of dipentaerythritol, cetyl caprate, glyceryl tricaprate, diisostearyl malate, dioctyl succinate, and cetyl 2-ethylhexanoate.

Specific examples of silicones include dimethylpolysiloxane (dimethicone), methylphenylpolysiloxane, decamethylcyclopentasiloxane, dodecamethylcyclohexasiloxane, terminal hydroxy-modified dimethylpolysiloxane, highly polymerized silicones having an average degree of polymerization of from 650 to 10,000, polyether-modified silicones, amino-modified silicones, betaine-modified silicones, alkyl-modified silicones, alkoxy-modified silicones, carboxy-modified silicones, and fluorine-modified silicones.

Specific examples of polyhydric alcohols include glycols and glycerols. Specific examples of glycols include ethylene glycol, diethylene glycol, triethylene glycol, polyethylene glycol, propylene glycol, dipropylene glycol, isoprene glycol, and 1,3-butylene glycol. Specific examples of glycerols include glycerol, diglycerol, and polyglycerol.

The surfactant used may be either an anionic or a cationic surfactant. An amphoteric surfactant other than the amphoteric surfactants having the structure represented by general formula (1) or a nonionic amphoteric surfactant other than sugar nonionic surfactants may be used.

Specific examples of anionic surfactants include alkyl ether sulfates, alkyl sulfates, alkenyl ether sulfates, alkenyl sulfates, olefin sulfonates, alkane sulfonates, saturated or unsaturated fatty acid salts, alkyl or alkenyl ether carboxylic acid salts, α-sulfone fatty acid salts, N-acylamino acid surfactants such as triethanolamine cocoyl glutamate (TEA cocoyl glutamate), phosphate mono- or diester surfactants, and sulfosuccinic acid esters. The counterions of the anionic groups on these surfactants are exemplified by sodium ions, potassium ions and triethanolamine ions. For example, sodium lauryl sulfate, which is a salt of an alkyl sulfuric acid, may be used.

Specific examples of cationic surfactants include lauryltrimethylammonium chloride, cetyltrimethylammonium chloride (cetrimonium chloride), stearyltrimethylammonium chloride (stearyltrimonium chloride), alkyltrimethylammonium chloride, distearyldimethylammonium chloride, behenyltrimethylammonium chloride (behentrimonium chloride), distearyldimethylammonium chloride (distearyldimonium chloride), cetyltrimethylammonium bromide, stearyltrimethylammonium bromide, lanolin fatty acid aminopropylethyldimethylammonium ethyl sulfate, stearyltrimethylammonium saccharin, cetyltrimethylammonium saccharin, methacryloyloxyethyltrimethylammonium chloride, behenyltrimethylammonium methyl sulfate, and quaternium-91.

Specific examples of amphoteric surfactants other than amphoteric surfactants having the structure represented by general formula (1) include coco betaine, lauramidopropyl betaine, cocamidopropyl betaine, sodium lauroamphoacetate, sodium cocoamphoacetate, and lauryl betaine (lauryl dimethylaminoacetic acid betaine).

Specific examples of nonionic surfactants other than sugar nonionic surfactants include ether nonionic surfactants and ester nonionic surfactants.

Specific examples of ether nonionic surfactants include POE cetyl ether (ceteth), POE stearyl ether (steareth), POE behenyl ether, POE oleyl ether (oleth), POE lauryl ether (laureth), POE octyl dodecyl ether, POE hexyl decyl ether, POE isostearyl ether, POE nonyl phenyl ether, POE octyl phenyl ether, and POE cetyl stearyl diether.

Specific examples of ester nonionic surfactants include POE glyceryl monostearate, POE glyceryl monomyristate, polyethylene glycol monooleate, polyethylene glycol monostearate, polyethylene glycol monolaurate, lipophilic glyceryl monooleate, lipophilic glyceryl monostearate, self-emulsifying glyceryl monostearate, decaglyceryl monolaurate, decaglyceryl monostearate, decaglyceryl monooleate, decaglyceryl monomyristate, and polyglyceryl laurate.

Specific examples of sugars include sorbitol, maltose, and glycosyl trehalose.

Specific examples of preservatives include sodium benzoate, methyl paraben, and phenoxyethanol.

Specific examples of stabilizers include phenacetin, 8-hydroxyquinoline, acetanilide, sodium pyrophosphate, barbituric acid, uric acid, and tannic acid.

Specific examples of pH adjustors include lactic acid, levulinic acid, glycolic acid, tartaric acid, malic acid, pyrrolidonecarboxylic acid (PCA), succinic acid, citric acid, glutamic acid, 2-amino-2-methyl-1-propanol (AMP), and triethanolamine (TEA).

Specific examples of plant and microbial extracts include hydrolyzed yeast extracts having a moisture-retaining effect.

Specific examples of protein hydrolyzates include (dihydroxymethylsilylpropoxy)hydroxypropyl-hydrolyzed collagen and hydroxypropyltrimonium-hydrolyzed wheat protein.

Specific examples of antioxidants include ascorbic acid and sulfites.

Specific examples of chelating agents include ethylenediaminetetraacetic acid (EDTA), diethylenetriaminepentaacetic acid and salts thereof, and hydroxyethanediphosphonic acid (HEDP, etidronic acid), and salts thereof.

Specific examples of inorganic salts include sodium chloride and sodium carbonate.

The hair-treatment composition may additionally include at least one type of ingredient selected from among those listed in "Japanese Standards of Quasi-Drug Ingredients" (published June 2006 by Yakuji Nippo, Ltd.).

Examples of the form of the hair-treatment composition include, but are not limited to, aqueous solutions, dispersions, emulsions, gels, foams, and creams.

The hair-treatment composition is used to suppress color fading in hair which has been dyed using an oxidative hair dye.

The oxidative hair dye is composed of a first agent containing an oxidation dye and an alkali agent, and a second agent containing an oxidizing agent. Oxidative hair dyes are prepared by mixing the first agent and the second agent at the time of use.

The oxidation dye contained in the first agent of the oxidative hair dye undergoes color development due to oxidative polymerization by the oxidizing agent contained in the second agent of the oxidative hair dye, and contains at least a dye intermediate. The oxidation dye may include also a coupler in addition to the dye intermediate.

Specific examples of the dye intermediate include phenylenediamines (exclusive of m-phenylenediamine), aminophenols (exclusive of m-aminophenol, 2,4-diaminophenol and p-methylaminophenol), toluylenediamines (exclusive of toluene-3,4-diamine and toluene-2,4-diamine), diphenylamines, diaminophenylamines, N-phenylphenylenediamines, diaminopyridines (exclusive of 2,6-diaminopyridine), and salts thereof, such as chlorides, sulfates, and acetates. The dye intermediates used may be of a single type, or two or more types of dye intermediates may be used in combination.

The coupler induces color development by coupling with the dye intermediate. Specific examples of couplers include resorcinol, pyrogallol, catechol, m-aminophenol, m-phenylenediamine, 2,4-diaminophenol, 1,2,4-benzenetriol, toluene-3,4-diamine, toluene-2,4-diamine, hydroquinone, α-naphthol, 2,6-diaminopyridine, 1,5-dihydroxynaphthalene, 5-amino-o-cresol, p-methylaminophenol, 2,4-diaminophenoxyethanol, gallic acid, tannic acid, ethyl gallate, methyl gallate, propyl gallate, nutgall, 5-(2-hydroxyethylamino)-2-methylphenol, and salts thereof. The coupler used may be of a single type, or two or more types of couplers may be used in combination.

An oxidative dye containing a dye intermediate and a coupler is preferably used on account of the ability to change the color tone of the hair as desired.

The content of dye intermediate in the oxidative hair dye is preferably from 0.01 to 10% by mass, and more preferably from 0.1 to 5% by mass. When the content of the dye intermediate is below 0.01% by mass, it may not be possible to sufficiently dye the hair. A dye intermediate content in excess of 10% by mass is not cost-effective.

The coupler content in the oxidative hair dye is preferably from 0.01 to 5% by mass, and more preferably from 0.1 to 3% by mass. When the content of the coupler content is below 0.01% by mass, it may not be possible to sufficiently dye the hair. A coupler content in excess of 5% by mass is not cost-effective.

The first agent of the oxidative hair dye may additionally include an oxidation dye listed in "Japanese Standards of Quasi-Drug Ingredients" (published June 2006 by Yakuji Nippo, Ltd.), or may additionally include a direct dye.

The alkali agent contained in the first agent of the oxidative hair dye promotes the action of the oxidizing agent contained in the second agent of the oxidative hair dye and also, by causing the hair to swell and improving penetration of the dye into the hair, improves the dyeability of the hair by the oxidative hair dye. Specific examples of the alkali agent used include ammonia, alkanolamines, organic amines, inorganic alkalis, basic amino acids, and salts thereof. Specific examples of organic amines include 2-amino-2-methyl-1,3-propanediol and guanidine. Specific examples of inorganic alkalis include sodium hydroxide, potassium hydroxide, sodium carbonate, and potassium carbonate. Specific examples of basic amino acids include arginine and lysine. Specific examples of salts include ammonium salts. The alkali agent used may be of only one type, or two or more types of alkali agents may be used in combination.

The alkali agent is preferably contained in the first agent in an amount such as to render the pH of the first agent of the oxidative hair dye in a range of from 8 to 12. In the case where the pH of the first agent pH is below 8, when the first agent and second agent are mixed, the action of the oxidizing agent, especially hydrogen peroxide, contained in the second agent may not be sufficiently promoted. At a first agent pH above 12, the hair tends to become damaged when the oxidative hair dye is applied thereto.

The content of the alkali agent in the first agent of the oxidative hair dye is preferably from 0.1 to 12% by mass, more preferably from 0.2 to 11% by mass, even more preferably from 0.6 to 10% by mass, and most preferably from 0.6 to 9% by mass. When the content of the alkali agent content is below 0.1% by mass, it may not be possible to uniformly dye the hair with the oxidative hair dye. When the content of the alkali agent is in excess of 12% by mass, the hair may not have a good tactile feel following treatment with the oxidative hair dye.

The first agent of the oxidative hair dye additionally contains a predetermined amount of water, and is prepared as an emulsion, a solution, or a dispersion. The water content in the first agent is preferably from 50 to 95% by mass, and more preferably from 70 to 90% by mass. When the content of water is below 50% by mass, it may be difficult to prepare the first agent as an emulsion, a solution, or a dispersion. When the content of water is in excess of 95% by mass, it may be difficult to ensure the uniformity and stability of the first agent.

Where necessary, the first agent of the oxidative hair dye may further include at least one type of additive selected from among, for example, oil-based ingredients, surfactants, water-soluble polymeric compounds, polyhydric alcohols, sugars, preservatives, chelating agents, stabilizers, pH adjustors, plant and microbial extracts, crude drug extracts, vitamins, fragrances, and ultraviolet absorbers. Some of the details concerning these ingredients duplicate the description given of the hair-treatment composition and thus are omitted here.

The form of the first agent of the oxidative hair dye is not particularly limited, and may be, for example, an aqueous solution, a dispersion, an emulsion, a gel, a foam, or a cream.

The oxidizing agent contained in the second agent of the oxidative hair dye induces color development by oxidatively polymerizing the oxidation dye contained in the first agent. Examples of the oxidizing agent used include hydrogen peroxide, urea peroxide, melamine peroxide, sodium percarbonate, potassium percarbonate, sodium perborate, potassium perborate, sodium peroxide, potassium peroxide, magnesium peroxide, barium peroxide, calcium peroxide, strontium peroxide, the hydrogen peroxide adducts of sulfates, the hydrogen peroxide adducts of phosphates, and the hydrogen peroxide adducts of pyrophosphates. The oxidizing agent used may be of only one type, or two or more types of oxidizing agents may be used in combination. Hydrogen peroxide is preferred as the oxidizing agent because it has an excellent ability to decolorize the melanin contained in hair.

The content of the oxidizing agent in the second agent of the oxidative hair dye is preferably from 0.1 to 10.0% by mass, and more preferably from 0.5 to 8.0% by mass. When the content of the oxidizing agent is below 0.1% by mass, it may be difficult to sufficiently oxidatively polymerize the oxidation dye contained in the first agent. When the content of the oxidizing agent is in excess of 10.0% by mass, the hair tends to be easily damaged by the oxidative hair dye.

Where necessary, the second agent of the oxidative hair dye may further include at least one type of additive selected from among water, oil-based ingredients, surfactants, water-soluble polymeric compounds, polyhydric alcohols, sugars, preservatives, chelating agents, stabilizers, pH adjustors, plant and microbial extracts, crude drug extracts, vitamins, fragrances, and ultraviolet absorbers. Some of the details concerning these ingredients duplicate the description given of the hair-treatment composition and thus are omitted here. The second agent may additionally include at least one type of ingredient selected from among those listed in "Japanese Standards of Quasi-Drug Ingredients" (published June 2006 by Yakuji Nippo, Ltd.).

The form of the second agent of the oxidative hair dye is not subject to any particular limitation, and may be, for example, an aqueous solution, a dispersion, an emulsion, a gel, a foam, or a cream.

The oxidative hair dye is applied to the hair and thereby used to color the hair. Oxidative hair dye that has been applied to the hair is rinsed off with, for example, warm water.

The above described hair-treatment composition of the embodiment may be applied to hair that has been dyed using an oxidative hair dye for the purpose of suppressing color fading in the hair. In other words, the hair-treatment composition may be used in the post-treatment of hair that has been dyed using an oxidative hair dye. The hair-treatment composition is preferably applied to hair in a wet state immediately after the hair is dyed with an oxidative hair dye; that is, to hair which is not dried and remains in a wet state after having been dyed with an oxidative hair dye. This enables the color tone of the hair immediately after dyeing to be easily maintained.

Hair to which the hair-treatment composition has been applied following dyeing with an oxidative hair dye can, after being washed and dried, have the same hair-treatment composition again applied thereto. In such a case, color fading of the dyed hair can be even further suppressed. After being dyed, the hair may be dried with a hair dryer or may be air-dried.

The embodiment described above in detail achieves the following advantages.

Since the hair-treatment composition of this embodiment contains a sugar nonionic surfactant in addition to an amphoteric surfactant having the structure indicated by general formula (1), it has high foaming properties and also strongly suppresses color fading in dyed hair. The reason that color fading in dyed hair is strongly suppressed by the hair-treatment composition is presumably because the amphoteric surfactant and the sugar nonionic surfactant contained in the hair-treatment composition protect the hair surface, helping to prevent the release of dye from the hair.

When the sugar nonionic surfactant contained in the hair-treatment composition is at least one selected from among sugar ester surfactants and alkyl glucosides, further improvements are achieved in the foaming properties of the hair-treatment composition and in the color fade suppressing effects by the hair-treatment composition on dyed hair.

Hair which has been dyed with an oxidizing hair dye generally undergoes greater damage than hair which has been dyed with an acidic hair color (hair manicure). In the case of hair which is strongly damaged in this way, unless the hair-treatment composition has high foaming properties, it does not conform well to the hair, making the composition difficult to apply. In this respect, because the hair-treatment composition of this embodiment has high foaming properties, it is easily applied to hair that has been dyed with an oxidative hair dye. Improving the foaming properties of the hair-treatment composition by including a foaming aid in the hair-treatment composition is also conceivable, although this may lower the color fade suppressing effect on dyed hair by the hair-treatment composition.

Because the hair-treatment composition of this embodiment has high foaming properties, it can conform well to hair. This lowers the frictional resistance between hairs, making treatment of the hair by the hair-treatment composition smoother.

The lather created by foaming of the hair-treatment composition is fine, which also helps the hair-treatment composition to conform to the hair.

Following treatment with the hair-treatment composition, the hair has good finger combing properties. This appears to be due to the adsorption to the hair of the amphoteric surfactant and the sugar nonionic surfactant contained in the hair-treatment composition.

The foregoing embodiment may be modified as follows.

The hair-treatment composition of the above embodiment is not limited to use on hair that has been dyed with an oxidative hair dye, and may be applied to hair that has been dyed with an acidic hair color (hair manicure). That is, to suppress color fade in hair dyed with an acidic hair color, the hair-treatment composition may be used in the post-treatment of the hair.

Hair to which the hair-treatment composition of the foregoing embodiment has been applied following dyeing of the hair with an oxidative hair dye may have the same hair-treatment composition repeatedly applied thereto daily or, for example, every 3 days, 5 days, or 7 days.

The hair-treatment composition of the above embodiment is not limited to single agent type compositions, and may instead be of a multiple agent type composed of a plurality of agents which are mixed together at the time of use. Alternatively, the plurality of agents making up a multiple agent type hair-treatment composition may be mixed on the hair itself by successive application to the hair.

The oxidative hair dye used in the foregoing embodiment is not limited to a two-agent type composition of a first agent and a second agent. For example, at least one of the first agent and the second agent may itself be composed of a plurality of agents which are mixed together at the time of use.

EXAMPLES

The invention will be illustrated in more detail below by way of examples thereof and comparative examples.

The shampoos (hair-treatment compositions) of Examples 1 to 5 and Comparative Examples 1 to 3 formulated as shown in Table 1 were prepared. In Table 1, the numerical values indicating the contents of the respective ingredients in the shampoos are in units of percent by mass.

<Evaluation of Lathering, Lather Fineness, and Finger Combing Properties>

Twenty panelists who felt they had severe hair damage and dry skin shampooed their own hair using the respective shampoos in Examples 1 to 5 and Comparative Examples 1 to 3, and rated the lathering properties and lather fineness of each shampoo. After washing their hair with the shampoo in each of Examples and Comparative Examples, the panelists applied a test hair conditioner to the hair and subsequently rinsed with warm water, then dried the hair and rated the finger combing properties of the hair both immediately after drying and 6 hours after drying. The test hair conditioner used contained 3% by mass of cetanol, 2.5% by mass of cetrimonium chloride, 0.2% by mass of glyceryl monostearate, 1% by mass of glycerol, 0.2% by mass of methyl paraben, and 0.2% by mass of fragrance, with the balance being purified water.

The lathering properties of the respective shampoos in Examples 1 to 5 and Comparative Examples 1 to 3 were rated as follows. Cases in which 17 or more of the panelists responded that the shampoo had good lathering properties were given a rating of "5"; cases in which 13 to 16 of the panelists responded in this way were given a rating of "4"; cases in which 9 to 12 of the panelists responded in this way were given a rating of "3"; cases in which 5 to 8 of the panelists responded in this way were given a rating of "2"; and cases in which 4 or fewer of the panelists responded in this way were given a rating of "1."

The fineness of the lather for the respective shampoos in Examples 1 to 5 and Comparative Examples 1 to 3 were rated as follows. Cases in which 17 or more of the panelists responded that the lather was fine were given a rating of "5"; cases in which 13 to 16 of the panelists responded in this way were given a rating of "4"; cases in which 9 to 12 of the panelists responded in this way were given a rating of "3"; cases in which 5 to 8 of the panelists responded in this way were given a rating of "2"; and cases in which 4 or fewer of the panelists responded in this way were given a rating of "1."

The finger combing properties of the hair after using the respective shampoos in Examples 1 to 5 and Comparative Examples 1 to 3 were rated as follows. When a test hair conditioner was applied to the hair then rinsed off and the hair dried, cases in which 17 or more of the panelists responded that the hair had good finger combing properties both immediately after drying and 6 hours after drying were given a rating of "5"; cases in which 13 to 16 of the panelists responded in this way were given a rating of "4"; cases in which 9 to 12 of the panelists responded in this way were given a rating of "3"; cases in which 5 to 8 of the panelists responded in this way were given a rating of "2"; and cases in which 4 or fewer of the panelists responded in this way were given a rating of "1."

These evaluation results are shown in the "lathering," "lather fineness," and "finger combing" columns in Table 1.

<Evaluation of Color Fade Suppressing Effect>

(1) Fabrication of Hair Bundle Samples for Testing

Bundles of black hair having a length of about 20 cm were prepared, and each bundle was decolorized by a conventional method using a decolorizing agent (available from Hoyu Co., Ltd. under the trade name "Promaster EX LT"). Each bundle was then washed with a test shampoo. A 10% by mass of aqueous solution of sodium laureth sulfate was used as the test shampoo. Each bundle was then subjected to permanent waving treatment by a conventional method using a permanent waving preparation (available from Hoyu Co., Ltd. under the trade name "Lutea TG"), then was washed again using the above test shampoo and dried. After drying, each bundle was dyed brown using an oxidative hair dye (available from Hoyu Co., Ltd. under the trade name "Promaster EX B 7/6"), thereby giving hair bundle samples for testing.

(2) Application of the Shampoos of the Working Examples and Comparative Examples Hair bundle samples for testing that were in a wet state after being dyed with an oxidative hair dye were then washed using the respective shampoos of Examples 1 to 5 and Comparative Examples 1 to 3. The above test hair conditioner was applied to each of the hair bundle samples and subsequently rinsed off with warm water, following which the hair was dried with a hair dryer. Hair bundle samples for testing which were subjected a total of ten times to the series of steps consisting of washing using the respective shampoos, applying and rinsing off the test hair conditioner, then drying, and hair bundle samples for testing which were subjected to the same series of steps only once were both prepared.

(3) Evaluation

The color tone of hair bundle samples for testing which were subjected a total of ten times to the series of steps consisting of washing using the respective shampoos of Examples 1 to 5 and Comparative Examples 1 to 3, subsequently applying and rinsing off the test hair conditioner, then drying was compared by the 20 panelists with the color tone of hair bundle samples for testing which were subjected to the same series of steps only once. Cases in which 17 or more of the panelists responded that there was no observable difference between the color tones of both, i.e., that color fade was not observable even when repeated washing was carried out with the respective shampoos, were given a rating of "5"; cases in which 13 to 16 of the panelists responded in this way were given a rating of "4"; cases in which 9 to 12 of the panelists responded in this way were given a rating of "3"; cases in which 5 to 8 of the panelists responded in this way were given a rating of "2"; and cases in which 4 or fewer of the panelists responded in this way were given a rating of "1." These evaluation results are shown in the "color fade suppression" column in Table 1.

The invention claimed is:

1. A hair-treatment composition applied to hair in a wet state immediately after the hair is dyed with an oxidative hair dye, comprising:
    (A) an amphoteric surfactant having a structure represented by the following general formula (1)

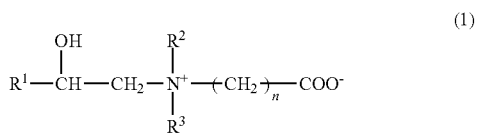

TABLE 1

|  |  | Examples | | | | | Comparative Examples | | |
| --- | --- | --- | --- | --- | --- | --- | --- | --- | --- |
|  |  | 1 | 2 | 3 | 4 | 5 | 1 | 2 | 3 |
| (A) | $C_{12-14}$ Hydroxyalkyl hydroxyethyl sarcosine | 2 | 2 | 2 | 2 | 2 | — | — | 2 |
|  | Sodium lauroyl sarcosine | — | — | — | — | — | — | 2 | — |
| (B) | Coconut oil alkyl glucoside | 2 | — | — | — | — | 2 | 2 | — |
| (B) | Octyl glucoside | — | 2 | — | — | — | — | — | — |
| (B) | Sucrose myristate | — | — | 2 | — | — | — | — | — |
| (B) | Sucrose laurate | — | — | — | 2 | — | — | — | — |
| (B) | Polysorbate-60 | — | — | — | — | 2 | — | — | — |
| Cocamidopropylbetaine | | 5 | 5 | 5 | 5 | 5 | 7 | 5 | 5 |
| TEA cocoyl glutamate | | 7 | 7 | 7 | 7 | 7 | 7 | 7 | 7 |
| Polyoxyethylene cetyl stearyl diether | | 0.5 | 0.5 | 0.5 | 0.5 | 0.5 | 0.5 | 0.5 | 0.5 |
| Polyglyceryl laurate-10 | | 1 | 1 | 1 | 1 | 1 | 1 | 1 | 2 |
| (PEG/PPG/butylene/dimethicone) copolymer | | 0.5 | 0.5 | 0.5 | 0.5 | 0.5 | 0.5 | 0.5 | 0.5 |
| Polyquaternium-10 | | 0.4 | 0.4 | 0.4 | 0.4 | 0.4 | 0.4 | 0.4 | 0.4 |
| Dipropylene glycol | | 5 | 5 | 5 | 5 | 5 | 5 | 5 | 5 |
| Ethanol | | 2 | 2 | 2 | 2 | 2 | 2 | 2 | 2 |
| Glycerol | | 2 | 2 | 2 | 2 | 2 | 2 | 2 | 2 |
| Sodium chloride | | 1.5 | 1.5 | 1.5 | 1.5 | 1.5 | 1.5 | 1.5 | 1.5 |
| Disodium edetate | | 0.05 | 0.05 | 0.05 | 0.05 | 0.05 | 0.05 | 0.05 | 0.05 |
| Etidronic acid | | 0.2 | 0.2 | 0.2 | 0.2 | 0.2 | 0.2 | 0.2 | 0.2 |
| Sodium benzoate | | 0.3 | 0.3 | 0.3 | 0.3 | 0.3 | 0.3 | 0.3 | 0.3 |
| Methyl paraben | | 0.2 | 0.2 | 0.2 | 0.2 | 0.2 | 0.2 | 0.2 | 0.2 |
| Fragrance | | 0.5 | 0.5 | 0.5 | 0.5 | 0.5 | 0.5 | 0.5 | 0.5 |
| Purified water | | balance | balance | balance | balance | balance | balance | balance | balance |
| Total | | 100 | 100 | 100 | 100 | 100 | 100 | 100 | 100 |
| Evaluation | Lathering | 5 | 5 | 5 | 5 | 5 | 3 | 3 | 2 |
|  | Lather fineness | 5 | 5 | 5 | 5 | 5 | 2 | 2 | 2 |
|  | Finger combing | 5 | 5 | 5 | 5 | 5 | 2 | 2 | 2 |
|  | Color fade suppression | 5 | 5 | 5 | 5 | 5 | 1 | 1 | 2 |

As shown in Table 1, in the shampoos of Examples 1 to 5, not only the ratings for lathering (i.e., foaming properties) and color fade suppression, but also the ratings for lather fineness and finger combing were all good.

By contrast, in the shampoo of Comparative Example 1, which did not contain a specific amphoteric surfactant, the shampoo of Comparative Example 2, which contained an anionic foaming agent instead of a specific amphoteric surfactant, and the shampoo of Comparative Example 3, which did not contain a sugar nonionic surfactant, the ratings for lathering and color fade suppression were inferior to those of the shampoos in the examples according to the invention. It was apparent from these results that the use of both an amphoteric surfactant and a sugar nonionic surfactant is essential for improving the ratings for lathering and color fade suppression.

(wherein $R^1$ represents an alkyl group the carbon number of which is 6 to 20; $R^2$ represents a methyl group, an ethyl group, or a hydroxyethyl group; $R^3$ represents a methyl group, an ethyl group, or a —$CH_2COOH$ group; and n is an integer from 1 to 3); and
    (B) a sugar nonionic surfactant.

2. The hair-treatment composition according to claim 1, wherein the sugar nonionic surfactant is of at least one type selected from the group consisting of sugar ester surfactants and alkyl glucosides.

3. A hair-treatment method comprising applying a hair-treatment composition to hair in a wet state immediately after the hair is dyed with an oxidative hair dye, wherein the hair-treatment composition comprises:
    (A) an amphoteric surfactant having a structure represented by the following general formula (1)

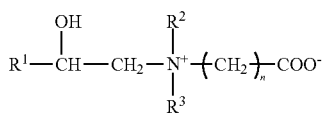 (1)

(wherein $R^1$ represents an alkyl group the carbon number of which is 6 to 20; $R^2$ represents a methyl group, an ethyl group, or a hydroxyethyl group; $R^3$ represents a methyl group, an ethyl group, or a —$CH_2COOH$ group; and n is an integer from 1 to 3); and (B) a sugar nonionic surfactant.

4. The hair-treatment method according to claim 3, further comprising, following application of the hair-treatment composition to hair:

washing and drying the hair; and applying the same hair-treatment composition again to the washed and dried hair.

* * * * *